(12) United States Patent
Hyakutake et al.

(10) Patent No.: US 10,030,274 B2
(45) Date of Patent: Jul. 24, 2018

(54) METHOD FOR SCREENING LACTIC ACID BACTERIA HAVING IMMUNOREGULATORY FUNCTION

(71) Applicant: ASAHI GROUP HOLDINGS, LTD., Tokyo (JP)

(72) Inventors: Sae Hyakutake, Kanagawa (JP); Tatsuhiko Hirota, Kanagawa (JP); Shinji Fukuda, Saitama (JP); Hiroshi Ohno, Saitama (JP); Naoyuki Yamamoto, Kanagawa (JP)

(73) Assignee: ASAHI GROUP HOLDINGS, LTD., Tokyo (JP)

( * ) Notice: Subject to any disclaimer, the term of this patent is extended or adjusted under 35 U.S.C. 154(b) by 130 days.

(21) Appl. No.: 14/762,038

(22) PCT Filed: Mar. 25, 2014

(86) PCT No.: PCT/JP2014/058308
§ 371 (c)(1),
(2) Date: Jul. 20, 2015

(87) PCT Pub. No.: WO2014/167995
PCT Pub. Date: Oct. 16, 2014

(65) Prior Publication Data
US 2015/0322496 A1  Nov. 12, 2015

(30) Foreign Application Priority Data

Apr. 11, 2013 (JP) .................................. 2013-083235
Dec. 9, 2013 (JP) .................................. 2013-254371

(51) Int. Cl.
*A23C 9/12* (2006.01)
*C12Q 1/689* (2018.01)
*G01N 33/569* (2006.01)
*A61K 35/747* (2015.01)
*C12R 1/23* (2006.01)
*C12N 1/20* (2006.01)
*C12R 1/225* (2006.01)
*C12Q 1/04* (2006.01)
*A23L 2/52* (2006.01)
*A23L 33/135* (2016.01)

(52) U.S. Cl.
CPC .............. *C12Q 1/689* (2013.01); *A23L 2/52* (2013.01); *A23L 33/135* (2016.08); *A61K 35/747* (2013.01); *C12N 1/20* (2013.01); *C12Q 1/04* (2013.01); *C12R 1/225* (2013.01); *C12R 1/23* (2013.01); *G01N 33/56911* (2013.01); *A23V 2002/00* (2013.01); *C12Q 2600/106* (2013.01); *C12Q 2600/136* (2013.01); *C12Q 2600/158* (2013.01); *G01N 2333/4703* (2013.01); *G01N 2400/00* (2013.01)

(58) Field of Classification Search
None
See application file for complete search history.

(56) References Cited

U.S. PATENT DOCUMENTS

| 2005/0214270 | A1 | 9/2005 | Yamamoto et al. | |
|---|---|---|---|---|
| 2006/0141546 | A1 | 6/2006 | Pugia et al. | |
| 2010/0022470 | A1* | 1/2010 | Wu ..................... | A61K 36/8984 514/54 |
| 2012/0122124 | A1* | 5/2012 | Biebl .................. | C07K 14/005 435/7.92 |
| 2012/0156760 | A1 | 6/2012 | Izumo et al. | |

FOREIGN PATENT DOCUMENTS

| EP | 1880726 A1 | 1/2008 |
|---|---|---|
| JP | 2004-26729 A | 1/2004 |
| JP | 2007-135587 A | 6/2007 |
| JP | 2007-143544 A | 6/2007 |
| JP | 2007-330157 A | 12/2007 |
| JP | 2010-158216 A | 7/2010 |
| WO | 20071052643 A1 | 5/2007 |
| WO | 20101110045 A1 | 9/2010 |

OTHER PUBLICATIONS

Shachner et al. Kidney international (1987) 31: 77-84.*
Toma et al. Biochem. Biophys. Research Comm. (1994) 2001(1): 275-282 (Year: 1994).*
Hase, et al., "Uptake through glycoprotein 2 of FimH+ bacteria by M cells initiates mucosal immune response", Nature, 2009, 462(12):226-231.
Borchers, et al., "Probiotics and immunity", Journal of Gastroenterol, 2009, 44:26-46.
Ishida, et al., "Decrease in ovalbumin specific IgE of mice serum after oral uptake of lactic acid bacteria", Biosci. Biotechnol. Biochem., 2003, 67(5):951-957.
Yamada, "Studies on the Development of Multifunctional Foods", Journal of Japan Society of Nutrition and Food Science, 2012, 65(2):59-64.
Pak, et al., "Tamm-Horsfall protein binds to type 1 fimbriated *Escherichia coli* and prevents *E. coli* from binding to uroplakin Ia and Ib receptors," Journal of Biological Chemistry, vol. 276, No. 13, Dec. 27, 2000, pp. 9924-9930.
European Patent Office, Extended European Search Report, dated Aug. 3, 2016 in connection with European Patent Application No. 14783317.2 (4 pages).
Sagitani, "Anti-allergic effects of Lactobacillus acidophilus L-92 strain", Japanese Journal of Lactic Acid Bacteria, 2010, vol. 21, No.3, pp. 207-213.
Plant et al., "The importance of an indigenous Lactobacillus population in colonization resistance of introduced strains", School of Microbiology and immunology, University of New South Wales, 2000.

(Continued)

*Primary Examiner* — Susan Marie Hanley
(74) *Attorney, Agent, or Firm* — Lucas & Mercanti, LLP

(57) ABSTRACT

This invention provides a means for screening for lactic acid bacteria having immunoregulatory functions in a simple and rapid manner. This invention provides a method for screening for or producing lactic acid bacteria having immunoregulatory functions comprising determining the number of the test lactic acid bacteria bound to the uromodulin (Umod) protein, lactic acid bacteria obtained by such method, and an immunoregulatory composition comprising such lactic acid bacteria.

10 Claims, 6 Drawing Sheets

(56) References Cited

OTHER PUBLICATIONS

Watanabe et al., "Development of 16s rRNA-targeted species-specific primers for Lactic Acid Bacteria in fermented milk products", Koichi Watanabe Yakult Central Institute for Microbiological Research. Culture Collection Center, 1997.
Japanese Office Action based on Japanese Application No. 2013-254371, dated Nov. 10, 2015. (4 pages).
"Lactobacillus fermentum 16s ribosomal RNA gene, complete sequence", GenBank, Oct. 10, 2000.
"Lactobacillus acidophilus gene for 16s rRNA, partial sequence, strain: YIT 0070 4356", GenBank, Dec. 28, 2007.

* cited by examiner

SEQUENCE LISTING

<160> NUMBER OF SEQ ID NOS: 19

<210> SEQ ID NO 1
<211> LENGTH: 515
<212> TYPE: DNA
<213> ORGANISM: Lactobacillus fermentum CP1299

<400> SEQUENCE: 1

```
atgcaagtcg aacgcgttgg cccaattgat tgatggtgct tgcacctgat tgattttggt      60
cgccaacgag tggcggacgg gtgagtaaca cgtaggtaac ctgcccagaa gcggggggaca    120 acatttggaa acagatgcta ataccgcata acaacgttgt tcgcatgaac aacgcttaaa    180
agatggcttc tcgctatcac ttctggatgg acctgcggtg cattagcttg ttggtggggt    240
aacggcctac caaggcgatg atgcatagcc gagttgagag actgatcggc cacaatggga    300
ctgagacacg gcccatactc ctacgggagg cagcagtagg gaatcttcca caatgggcgc    360
aagcctgatg gagcaacacc gcgtgagtga agaagggttt cggctcgtaa agctctgttg    420
ttaaagaaga acacgtatga gagtaactgt tcatacgttg acggtatttta accagaaagt    480 cacggctaac tacgtgccag cagccgcggt aatac                                515
```

<210> SEQ ID NO 2

<211> LENGTH: 504
<212> TYPE: DNA
<213> ORGANISM: Lactobacillus acidophilus CP1613

<400> SEQUENCE: 2

```
atgcaagtcg agcgagctga accaacagat tcacttcggt gatgacgttg ggaacgcgag      60
cggcggatgg gtgagtaaca cgtggggaac ctgccccata gtctgggata ccacttggaa     120
acaggtgcta ataccggata agaaagcaga tcgcatgatc agcttataaa aggcggcgta     180
agctgtcgct atgggatggc cccgcggtgc attagctagt tggtagggta acggcctacc     240
aaggcaatga tgcatagccg agttgagaga ctgatcggcc acattgggac tgagacacgg     300
cccaaactcc tacgggaggc agcagtaggg aatcttccac aatggacgaa agtctgatgg     360
agcaacgccg cgtgagtgaa gaaggttttc ggatcgtaaa gctctgttgt tggtgaagaa     420
ggatagaggt agtaactggc ctttatttga cggtaatcaa ccagaaagtc acggctaact     480
acgtgccagc agccgcggta atac                                            504
```

<210> SEQ ID NO 3
<211> LENGTH: 515
<212> TYPE: DNA
<213> ORGANISM: Lactobacillus fermentum CP1753

<400> SEQUENCE: 3

```
atgcaagtcg aacgcgttgg cccaattgat tgatggtgct tgcacctgat tgatttttggt     60
cgccaacgag tggcggacgg gtgagtaaca cgtaggtaac ctgcccagaa gcggggggaca    120
acatttggaa acagatgcta ataccgcata acagcgttgt tcgcatgaac aacgcttaaa    180
agatggcttc tcgctatcac ttctggatgg acctgcggtg cattagcttg ttggtggggt    240
aayggcctac caaggcgatg atgcatagcc gagttgagag actgatcggc cacaatggga    300
ctgagacacg gcccatactc ctacgggagg cagcagtagg gaatcttcca caatgggcgc    360
aagcctgatg gagcaacacc gcgtgagtga agaagggttt cggctcgtaa agctctgttg    420
ttaaagaaga acacgtatga gagtaactgt tcatacgttg acggtattta accagaaagt    480
cacggctaac tacgtgccag cagccgcggt aatac                               515
```

<210> SEQ ID NO 4
<211> LENGTH: 1929
<212> TYPE: DNA
<213> ORGANISM: Mus musculus
<220> FEATURE:
<221> NAME/KEY: CDS
<222> LOCATION: (1)..(1929)

<400> SEQUENCE: 4

```
atg ggg atc cct ttg acc tgg atg ctg ctg gta atg atg gta acc tcc      48
Met Gly Ile Pro Leu Thr Trp Met Leu Leu Val Met Met Val Thr Ser
1               5                  10                  15 tgg ttc act ctg gct gaa gcc agt aac tca aca gaa gcg aga cgg tgt      96
Trp Phe Thr Leu Ala Glu Ala Ser Asn Ser Thr Glu Ala Arg Arg Cys
            20                  25                  30 tct gaa tgc cac aac aac gcc acc tgc acg gtg gat ggt gtg gtc aca     144
Ser Glu Cys His Asn Asn Ala Thr Cys Thr Val Asp Gly Val Val Thr
        35                  40                  45 acg tgc tcc tgc cag acc ggc ttc act ggt gat ggg ctg gtg tgt gag     192
Thr Cys Ser Cys Gln Thr Gly Phe Thr Gly Asp Gly Leu Val Cys Glu
    50                  55                  60 gac atg gat gag tgt gct acc cca tgg act cac aac tgc tcc aac agc     240
Asp Met Asp Glu Cys Ala Thr Pro Trp Thr His Asn Cys Ser Asn Ser
```

```
                    65                  70                  75                  80
agc tgt gtg aac acc ccg ggc tcg ttt aag tgc tcc tgt cag gat ggt        288
Ser Cys Val Asn Thr Pro Gly Ser Phe Lys Cys Ser Cys Gln Asp Gly
                85                  90                  95 ttt cgt ctg acg cct gag ctg agc tgc act gat gtg gat gag tgc tca        336
Phe Arg Leu Thr Pro Glu Leu Ser Cys Thr Asp Val Asp Glu Cys Ser
            100                 105                 110 gag cag ggg ctc agt aac tgt cat gcc ctg gcc acc tgt gtc aac aca        384
Glu Gln Gly Leu Ser Asn Cys His Ala Leu Ala Thr Cys Val Asn Thr
        115                 120                 125 gaa ggc gac tac ttg tgc gtg tgt ccc gag ggc ttt aca ggg gat ggt        432
Glu Gly Asp Tyr Leu Cys Val Cys Pro Glu Gly Phe Thr Gly Asp Gly
    130                 135                 140 tgg tac tgt gag tgc tcc cca ggc tcc tgt gag cca gga ctg gac tgc        480
Trp Tyr Cys Glu Cys Ser Pro Gly Ser Cys Glu Pro Gly Leu Asp Cys
145                 150                 155                 160 ttg ccc cag ggc ccg gat gga aag ctg gtg tgt caa gac ccc tgc aat        528
Leu Pro Gln Gly Pro Asp Gly Lys Leu Val Cys Gln Asp Pro Cys Asn
                165                 170                 175 aca tat gag acc ctg act gag tac tgg cgc agc aca gag tat ggt gtg        576
Thr Tyr Glu Thr Leu Thr Glu Tyr Trp Arg Ser Thr Glu Tyr Gly Val
            180                 185                 190 ggc tac tcc tgt gac gcg ggt ctg cac ggc tgg tac cgg ttc aca ggc        624
Gly Tyr Ser Cys Asp Ala Gly Leu His Gly Trp Tyr Arg Phe Thr Gly
        195                 200                 205 cag ggt ggc gtt cgc atg gct gag acc tgt gtg ccc gtc ctg cga tgc        672
Gln Gly Gly Val Arg Met Ala Glu Thr Cys Val Pro Val Leu Arg Cys
    210                 215                 220 aac acg gcg gca ccc atg tgg ctc aat ggc tct cat ccc tcg agt agt        720
Asn Thr Ala Ala Pro Met Trp Leu Asn Gly Ser His Pro Ser Ser Ser
225                 230                 235                 240 gaa ggc att gtg agc cgc acg gcc tgt gca cac tgg agc gac caa tgc        768
Glu Gly Ile Val Ser Arg Thr Ala Cys Ala His Trp Ser Asp Gln Cys
                245                 250                 255 tgc cgg tgg tcc aca gag atc cag gtg aag gct tgc cca ggt ggc ttc        816
Cys Arg Trp Ser Thr Glu Ile Gln Val Lys Ala Cys Pro Gly Gly Phe
            260                 265                 270 tat att tac aac ttg aca gcg ccc cct gag tgc aat ctg gct tac tgc        864
Tyr Ile Tyr Asn Leu Thr Ala Pro Pro Glu Cys Asn Leu Ala Tyr Cys
        275                 280                 285 acc gat cct agt tcc gtg gag ggg act tgc gaa gaa tgc agg gta gat        912
Thr Asp Pro Ser Ser Val Glu Gly Thr Cys Glu Glu Cys Arg Val Asp
    290                 295                 300 gaa gat tgc ata tcg gat aac ggc aga tgg cgc tgc cag tgt aaa cag        960
Glu Asp Cys Ile Ser Asp Asn Gly Arg Trp Arg Cys Gln Cys Lys Gln
305                 310                 315                 320 gac tcc aac atc aca gat gtc tcc caa ttg gag tac agg ctg gag tgt        1008
Asp Ser Asn Ile Thr Asp Val Ser Gln Leu Glu Tyr Arg Leu Glu Cys
                325                 330                 335 ggg gcc aat gac atc aag atg tcc ctc aga aag tgc cag cta cag agt        1056
Gly Ala Asn Asp Ile Lys Met Ser Leu Arg Lys Cys Gln Leu Gln Ser
            340                 345                 350 ttg ggc ttt atg aat gtc ttc atg tac ctg aat gac aga caa tgc tca        1104
Leu Gly Phe Met Asn Val Phe Met Tyr Leu Asn Asp Arg Gln Cys Ser
        355                 360                 365 ggc ttc agt gag agt gat gaa cga gac tgg atg tcc ata gtg acc cct        1152
Gly Phe Ser Glu Ser Asp Glu Arg Asp Trp Met Ser Ile Val Thr Pro
    370                 375                 380 gcc agg aat ggt ccc tgt ggg aca gta ttg agg aga aac gaa acc cat        1200
```

```
                Ala Arg Asn Gly Pro Cys Gly Thr Val Leu Arg Asn Glu Thr His
                385             390                 395                 400 gcc acc tac agc aac acc ctc tac ctg gca aat gcg atc atc att cgg        1248
Ala Thr Tyr Ser Asn Thr Leu Tyr Leu Ala Asn Ala Ile Ile Ile Arg
                405                 410                 415 gac atc atc ata aga atg aac ttt gaa tgc tct tac cct ctg gac atg        1296
Asp Ile Ile Ile Arg Met Asn Phe Glu Cys Ser Tyr Pro Leu Asp Met
                420                 425                 430 aaa gtc agc ctg aag acc tcc cta cag ccc atg gtc agt gcc ctg aac        1344
Lys Val Ser Leu Lys Thr Ser Leu Gln Pro Met Val Ser Ala Leu Asn
                435                 440                 445 atc agc ttg ggt ggg aca ggc aag ttc acc gtg cgg atg gca ttg ttc        1392
Ile Ser Leu Gly Gly Thr Gly Lys Phe Thr Val Arg Met Ala Leu Phe
    450                 455                 460 cag agc cct acc tac aca cag ccc cac caa ggt cct tct gtg atg ctg        1440
Gln Ser Pro Thr Tyr Thr Gln Pro His Gln Gly Pro Ser Val Met Leu
465                 470                 475                 480 tcc act gag gct ttt ctg tat gtg ggc acc atg ctg gat ggg ggt gac        1488
Ser Thr Glu Ala Phe Leu Tyr Val Gly Thr Met Leu Asp Gly Gly Asp
                485                 490                 495 ttg tcc cgg ttt gta ctg cta atg acc aac tgc tat gcc aca ccc agt        1536
Leu Ser Arg Phe Val Leu Leu Met Thr Asn Cys Tyr Ala Thr Pro Ser
                500                 505                 510 agc aac tcc aca gac cct gtg aaa tac ttc att atc cag gac agt tgt        1584
Ser Asn Ser Thr Asp Pro Val Lys Tyr Phe Ile Ile Gln Asp Ser Cys
                515                 520                 525 cca cgt aca gaa gat aca acc att cag gtg aca gag aat ggc gag tca        1632
Pro Arg Thr Glu Asp Thr Thr Ile Gln Val Thr Glu Asn Gly Glu Ser
    530                 535                 540 tct cag gcc cga ttt tct gtt cag atg ttc cgg ttt gca gga aac tac        1680
Ser Gln Ala Arg Phe Ser Val Gln Met Phe Arg Phe Ala Gly Asn Tyr
545                 550                 555                 560 gac ctt gtc tac ctt cac tgc gag gtg tac cta tgt gac tct acg agt        1728
Asp Leu Val Tyr Leu His Cys Glu Val Tyr Leu Cys Asp Ser Thr Ser
                565                 570                 575 gaa cag tgt aaa cct acc tgc tct ggt act aga ttt cga agt ggg aac        1776
Glu Gln Cys Lys Pro Thr Cys Ser Gly Thr Arg Phe Arg Ser Gly Asn
                580                 585                 590 ttc ata gat cag acc cgt gtc ctg aac ttg ggt ccc ata aca cga caa        1824
Phe Ile Asp Gln Thr Arg Val Leu Asn Leu Gly Pro Ile Thr Arg Gln
                595                 600                 605 ggt gtc cag gcc tca gtg tcc aag gct gct tcc agc aac ttg agg ctc        1872
Gly Val Gln Ala Ser Val Ser Lys Ala Ala Ser Ser Asn Leu Arg Leu
    610                 615                 620 ctg agc atc tgg ctg ctg ttg ttt ccc tca gcc act ttg atc ttc atg        1920
Leu Ser Ile Trp Leu Leu Leu Phe Pro Ser Ala Thr Leu Ile Phe Met
625                 630                 635                 640 gtt caa tga                                                            1929
Val Gln <210> SEQ ID NO 5
<211> LENGTH: 642
<212> TYPE: PRT
<213> ORGANISM: Mus musculus

<400> SEQUENCE: 5

Met Gly Ile Pro Leu Thr Trp Met Leu Leu Val Met Met Val Thr Ser
1               5                   10                  15

Trp Phe Thr Leu Ala Glu Ala Ser Asn Ser Thr Glu Ala Arg Arg Cys
                20                  25                  30
```

```
Ser Glu Cys His Asn Asn Ala Thr Cys Thr Val Asp Gly Val Val Thr
         35                  40                  45
Thr Cys Ser Cys Gln Thr Gly Phe Thr Gly Asp Gly Leu Val Cys Glu
     50                  55                  60
Asp Met Asp Glu Cys Ala Thr Pro Trp Thr His Asn Cys Ser Asn Ser
 65                  70                  75                  80
Ser Cys Val Asn Thr Pro Gly Ser Phe Lys Cys Ser Cys Gln Asp Gly
                 85                  90                  95
Phe Arg Leu Thr Pro Glu Leu Ser Cys Thr Asp Val Asp Glu Cys Ser
             100                 105                 110
Glu Gln Gly Leu Ser Asn Cys His Ala Leu Ala Thr Cys Val Asn Thr
             115                 120                 125
Glu Gly Asp Tyr Leu Cys Val Cys Pro Glu Gly Phe Thr Gly Asp Gly
         130                 135                 140
Trp Tyr Cys Glu Cys Ser Pro Gly Ser Cys Glu Pro Gly Leu Asp Cys
145                 150                 155                 160
Leu Pro Gln Gly Pro Asp Gly Lys Leu Val Cys Gln Asp Pro Cys Asn
                 165                 170                 175
Thr Tyr Glu Thr Leu Thr Glu Tyr Trp Arg Ser Thr Glu Tyr Gly Val
             180                 185                 190
Gly Tyr Ser Cys Asp Ala Gly Leu His Gly Trp Tyr Arg Phe Thr Gly
         195                 200                 205
Gln Gly Gly Val Arg Met Ala Glu Thr Cys Val Pro Val Leu Arg Cys
     210                 215                 220
Asn Thr Ala Ala Pro Met Trp Leu Asn Gly Ser His Pro Ser Ser Ser
225                 230                 235                 240
Glu Gly Ile Val Ser Arg Thr Ala Cys Ala His Trp Ser Asp Gln Cys
                 245                 250                 255
Cys Arg Trp Ser Thr Glu Ile Gln Val Lys Ala Cys Pro Gly Gly Phe
             260                 265                 270
Tyr Ile Tyr Asn Leu Thr Ala Pro Pro Glu Cys Asn Leu Ala Tyr Cys
         275                 280                 285
Thr Asp Pro Ser Ser Val Glu Gly Thr Cys Glu Glu Cys Arg Val Asp
     290                 295                 300
Glu Asp Cys Ile Ser Asp Asn Gly Arg Trp Arg Cys Gln Cys Lys Gln
305                 310                 315                 320
Asp Ser Asn Ile Thr Asp Val Ser Gln Leu Glu Tyr Arg Leu Glu Cys
                 325                 330                 335
Gly Ala Asn Asp Ile Lys Met Ser Leu Arg Lys Cys Gln Leu Gln Ser
             340                 345                 350
Leu Gly Phe Met Asn Val Phe Met Tyr Leu Asn Asp Arg Gln Cys Ser
         355                 360                 365
Gly Phe Ser Glu Ser Asp Glu Arg Asp Trp Met Ser Ile Val Thr Pro
     370                 375                 380
Ala Arg Asn Gly Pro Cys Gly Thr Val Leu Arg Arg Asn Glu Thr His
385                 390                 395                 400
Ala Thr Tyr Ser Asn Thr Leu Tyr Leu Ala Asn Ala Ile Ile Ile Arg
                 405                 410                 415
Asp Ile Ile Ile Arg Met Asn Phe Glu Cys Ser Tyr Pro Leu Asp Met
             420                 425                 430
Lys Val Ser Leu Lys Thr Ser Leu Gln Pro Met Val Ser Ala Leu Asn
         435                 440                 445
```

-continued

```
Ile Ser Leu Gly Gly Thr Gly Lys Phe Thr Val Arg Met Ala Leu Phe
450                 455                 460

Gln Ser Pro Thr Tyr Thr Gln Pro His Gln Gly Pro Ser Val Met Leu
465                 470                 475                 480

Ser Thr Glu Ala Phe Leu Tyr Val Gly Thr Met Leu Asp Gly Gly Asp
                485                 490                 495

Leu Ser Arg Phe Val Leu Leu Met Thr Asn Cys Tyr Ala Thr Pro Ser
            500                 505                 510

Ser Asn Ser Thr Asp Pro Val Lys Tyr Phe Ile Ile Gln Asp Ser Cys
        515                 520                 525

Pro Arg Thr Glu Asp Thr Thr Ile Gln Val Thr Glu Asn Gly Glu Ser
530                 535                 540

Ser Gln Ala Arg Phe Ser Val Gln Met Phe Arg Phe Ala Gly Asn Tyr
545                 550                 555                 560

Asp Leu Val Tyr Leu His Cys Glu Val Tyr Leu Cys Asp Ser Thr Ser
                565                 570                 575

Glu Gln Cys Lys Pro Thr Cys Ser Gly Thr Arg Phe Arg Ser Gly Asn
            580                 585                 590

Phe Ile Asp Gln Thr Arg Val Leu Asn Leu Gly Pro Ile Thr Arg Gln
        595                 600                 605

Gly Val Gln Ala Ser Val Ser Lys Ala Ala Ser Ser Asn Leu Arg Leu
610                 615                 620

Leu Ser Ile Trp Leu Leu Leu Phe Pro Ser Ala Thr Leu Ile Phe Met
625                 630                 635                 640

Val Gln

<210> SEQ ID NO 6
<211> LENGTH: 30
<212> TYPE: DNA
<213> ORGANISM: Artificial
<220> FEATURE:
<223> OTHER INFORMATION: Primer

<400> SEQUENCE: 6
cgcagatcta ccatggggat ccctttgacc                                      30

<210> SEQ ID NO 7
<211> LENGTH: 28
<212> TYPE: DNA
<213> ORGANISM: Artificial
<220> FEATURE:
<223> OTHER INFORMATION: Primer

<400> SEQUENCE: 7
cgcgtcgacc ttggacactg aggcctgg                                        28

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
aactggagga aggtggggat                                                 20

<210> SEQ ID NO 9
<211> LENGTH: 19
<212> TYPE: DNA
<213> ORGANISM: Artificial
```

```
<220> FEATURE:
<223> OTHER INFORMATION: primer

<400> SEQUENCE: 9
aggaggtgat ccaaccgca                                                19

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
ccccagctag ttgtcatcct g                                             21

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
cgcatccgtg gatatggctc                                               20

<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
acagccggga agacaataac t                                             21

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
gcagctctag gagcatgtgg                                               20

<210> SEQ ID NO 14
<211> LENGTH: 22
<212> TYPE: DNA
<213> ORGANISM: Artificial
<220> FEATURE:
<223> OTHER INFORMATION: primer

<400> SEQUENCE: 14
caatcacgct acctcctctt tt                                            22

<210> SEQ ID NO 15
<211> LENGTH: 23
<212> TYPE: DNA
<213> ORGANISM: Artificial
<220> FEATURE:
<223> OTHER INFORMATION: primer

<400> SEQUENCE: 15
cagcagtgca ggaataatgt ttc                                           23
```

```
<210> SEQ ID NO 16
<211> LENGTH: 21
<212> TYPE: DNA
<213> ORGANISM: Artificial
<220> FEATURE:
<223> OTHER INFORMATION: primer

<400> SEQUENCE: 16
aggtcggtgt gaacggattt g                                    21

<210> SEQ ID NO 17
<211> LENGTH: 19
<212> TYPE: DNA
<213> ORGANISM: Artificial
<220> FEATURE:
<223> OTHER INFORMATION: primer

<400> SEQUENCE: 17
ggggtcgttg atggcaaca                                       19

<210> SEQ ID NO 18
<211> LENGTH: 19
<212> TYPE: DNA
<213> ORGANISM: Artificial
<220> FEATURE:
<223> OTHER INFORMATION: primer

<400> SEQUENCE: 18
agctggtgaa acggaagcg                                       19

<210> SEQ ID NO 19
<211> LENGTH: 21
<212> TYPE: DNA
<213> ORGANISM: Artificial
<220> FEATURE:
<223> OTHER INFORMATION: primer

<400> SEQUENCE: 19
gcgagcctta gtttggacag g                                    21
```

METHOD FOR SCREENING LACTIC ACID BACTERIA HAVING IMMUNOREGULATORY FUNCTION

CROSS-REFERENCE TO RELATED APPLICATIONS

This application is a 371 of PCT/JP2014/058308, filed Mar. 25, 2014, which claims the benefit of Japanese Patent Application Nos. 2013-083235, filed Apr. 11, 2013 and 2013-254371, filed Dec. 9, 2013.

TECHNICAL FIELD

The present invention relates to a method for screening for lactic acid bacteria having immunoregulatory functions, lactic acid bacteria obtained by such method, and an immunoregulatory composition containing such lactic acid bacteria.

BACKGROUND ART

The number of patients with allergies, such as atopic dermatitis and pollinosis, is increasing every year. According to the results of the investigation conducted by the Ministry of Health, Labour and Welfare of Japan, one in three people have an allergic disease of some kind in Japan. As causes of the increase in allergic diseases in recent years, increased allergens, such as pollens and mites, environmental pollution, an increase in intake of protein due to the Westernization of dietary habits, a change in intestinal bacterial environment, stress, and a decrease in infection by bacteria and parasites (i.e., the hygiene hypothesis) are illustrated. Along with allergic diseases, inflammatory bowel diseases are rapidly increasing in Japan, such diseases are closely related to the intestinal environment, and, as causes of development of such diseases, disturbance in the intestinal environment and abnormalities in the gut immune system in which type II helper T cells (Th2) become dominant over type I helper T cells (Th1), have been suggested.

The intestinal tract comprises gut-associated lymphoid tissue (GALT) composed of, for example, the Payer's patch (PP), the lamina propria (LP), the lamina propria lymphocytes (LPL), the intraepithelial lymphocytes (IEL), the intestinal epithelial cells (IEC), and the cryptopatch (CP), and the intestinal tract functions as the greatest immune organ in the body. In particular, microfold cells (M cells) existing in the follicle-associated epithelium (FAE) that covers the lumen side of the Payer's patch are specialized in antigen uptake, and M cells play a key role in the induction of immune responses of the intestinal tract. The molecular mechanism associated with antigen uptake from the M cells has gradually been elucidated. As GP2 expressed in M cells binds to the bacterial antigen or the like, the antigen is transferred to the immunocytes (e.g., antigen-presenting cells, B cells, and T cells) existing inside the Payer's patch, and various immune responses, such as the production of IgA antibody or cytokines, take place (Non-Patent Document 1).

As described above, allergic diseases and inflammatory bowel diseases are considered to result from disorders in the gut immune system. Accordingly, it is considered effective for the gut immune system to be activated in order to normally function, so that the diseases described above would be treated and prevented. To date, a variety of food raw materials that can control the intestinal environment and improve the gut immune system have been examined, and lactic acid bacteria are among the most effective food components. It has actually been reported that the immune balance is improved with the administration of lactic acid bacteria and that lactic acid bacteria are effective for improvement of allergic diseases and inflammatory bowel diseases (Non-Patent Document 2). However, the effects of lactic acid bacteria vary depending on the type thereof, and lactic acid bacteria with stronger immunoregulatory functions, such as anti-allergic functions, have been desired for probiotic food.

In order to utilize lactic acid bacteria exerting various functions, such as immunoregulatory functions, intestinal regulation functions (e.g., acceleration of intestinal peristalsis, regulation of intestinal flora balance, remediation of diarrhea and/or constipation, and stool odor reduction), life-extending actions, improvement of nutrient digestion and absorption, anti-aging actions, pathogen-eliminating actions, cholesterol-lowering actions, stress relief, cutaneous function improvement, beauty effects, anti-inflammatory actions, cancer inhibition, and dental caries prevention, it is necessary to conduct clinical trials involving human subjects so as to verify the functions of such lactic acid bacteria. To this end, a means for primary screening of useful lactic acid bacteria in a more simple and rapid manner is necessary. Up to the present, methods for screening for lactic acid bacteria, such as methods involving the use of animal models of allergic diseases (Patent Document 1 and Non-Patent Document 3) and methods involving the use of cultured cells (Patent Documents 2 and 3) have been known. However, screening methods involving the use of disease animal models are time consuming, they necessitate laborious procedures, and it is difficult to prepare many test groups. Also, the results attained for the established cell lines that are frequently used for a screening method involving the use of cultured cells cannot always be reproduced with primary cultured cells. In addition, inherent regulatory mechanisms may occasionally be denatured during the process of cell establishment, and, disadvantageously, in vivo reactions are not always reflected (Non-Patent Document 4). Therefore, a method that can be used to extensively screen for lactic acid bacterial strains with strong immunoregulatory functions from many lactic acid bacterial strains in vitro in a simple and rapid manner and with a single operation has been awaited.

PRIOR ART DOCUMENTS

Patent Documents

Patent Document 1: JP 2007-135587 A
Patent Document 2: JP 2007-143544 A
Patent Document 3: JP 2007-330157 A Non-Patent Documents Non-Patent Document 1: Hase K. et al., Uptake through glycoprotein 2 of FimH1 bacteria by M cells initiates mucosal immune response, Nature 2009, 462: 226-231

Non-Patent Document 2: Borchers, A. T. et al., Probiotics and immunity, J. Gastroenterol., 2009, 44, 26-46

Non-Patent Document 3: Ishida Y. et al., Decrease in Ovalbumin Specific IgE of Mice Serum after Oral Uptake of Lactic Acid Bacteria, Biosci. Biotechnol. Biochem., 2003, 67: 951

Non-Patent Document 4: Koji Yamada, the Journal of Japan Society of Nutrition and Food Science, Vol. 65, No. 2, pp. 59-64, 2012, Research on Development of Multifunctional Food

SUMMARY OF THE INVENTION

Problem to be Solved by the Invention

It is an object of the present invention to provide a means for screening for lactic acid bacteria having immunoregulatory functions in a simple and rapid manner.

Means for Solving the Problem

The present inventors have conducted concentrated studies in order to attain the above object. They focused on a uromodulin (Umod) protein (hereafter, it is occasionally referred to simply as "Umod") expressed in M cells in the epithelial cell layer of the Payer's patch in the small intestine and inspected the number of lactic acid bacteria bound to Umod in vitro. As a result, they discovered that lactic acid bacteria exhibiting the large number of bonds would suppress IgE production in vivo, such lactic acid bacteria would suppress the production of Th2 cytokines (IL-4 and IL-10) in the mesenteric lymph nodes, and such lactic acid bacteria would enhance the production of Th1 cytokine (IL-12) and anti-inflammatory cytokine TGF-β. Specifically, the present inventors discovered that lactic acid bacteria having strong immunoregulatory functions could be screened for in vitro by employing the number of lactic acid bacteria bound to Umod as an indicator. This has led to the completion of the present invention.

Specifically, the present invention encompasses the following.

[1] A method for screening for lactic acid bacteria having immunoregulatory functions comprising determining the number of test lactic acid bacteria bound to a uromodulin (Umod) protein.

[2] The screening method according to [1], wherein test lactic acid bacteria having immunoregulatory functions are selected when the number of the test lactic acid bacteria bound to the uromodulin (Umod) protein is larger than or equivalent to the number of the *Lactobacillus acidophilus* CL-92 strain bound to the uromodulin (Umod) protein.

[3] A method for screening for lactic acid bacteria having immunoregulatory functions comprising the following steps:

(a) bringing test lactic acid bacteria into contact with a uromodulin (Umod) protein;

(b) determining the number of the test lactic acid bacteria bound to the uromodulin (Umod) protein;

(c) comparing the number of bonds determined in (b) with the number of the *Lactobacillus acidophilus* CL-92 strain bound to the uromodulin (Umod) protein (control number of bonds); and (d) selecting lactic acid bacteria exhibiting the number of bonds larger than or equivalent to the control number of bonds as lactic acid bacteria having immunoregulatory functions from among the test lactic acid bacteria based on the results of (c).

[4] The method according to any one of [1] to [3], wherein the number of bonds is determined based on the gene amount of the lactic acid bacteria bound to the uromodulin (Umod) protein.

[5] A method for evaluating the immunoregulatory functions of lactic acid bacteria comprising comparing the number of the test lactic acid bacteria bound to the uromodulin (Umod) protein with the number of the *Lactobacillus acidophilus* CL-92 strain bound to the uromodulin (Umod) protein, and evaluating the immunoregulatory functions of the test lactic acid bacteria.

[6] A method for producing lactic acid bacteria having immunoregulatory functions comprising the following steps:

(a) bringing test lactic acid bacteria into contact with a uromodulin (Umod) protein;

(b) determining the number of the test lactic acid bacteria bound to the uromodulin (Umod) protein;

(c) comparing the number of bonds determined in (b) with the number of the *Lactobacillus acidophilus* CL-92 strain bound to the uromodulin (Umod) protein (control number of bonds); and (d) selecting lactic acid bacteria exhibiting the number of bonds larger than or equivalent to the control number of bonds as lactic acid bacteria having immunoregulatory functions from among the test lactic acid bacteria based on the results of (c).

[7] Lactic acid bacteria having immunoregulatory functions, wherein the number of the bacteria bound to the uromodulin (Umod) protein is larger than or equivalent to the number of the *Lactobacillus acidophilus* CL-92 strain bound to the uromodulin (Umod) protein.

[8] Lactic acid bacteria having immunoregulatory functions obtained by the method according to [6].

[9] The *Lactobacillus fermentum* CP1299 strain identified by Accession Number NITE BP-1512, the *Lactobacillus acidophilus* CP1613 strain identified by Accession Number NITE BP-1513, the *Lactobacillus fermentum* CP1753 strain identified by Accession Number NITE BP-1514, or an analog or variant of any thereof.

[10] An immunoregulatory composition comprising, as an active ingredient, the lactic acid bacteria according to any one of [7] to [9].

[11] The immunoregulatory composition according to [10], which is a medicine.

[12] The immunoregulatory composition according to [10], which is a food or beverage product.

[13] Use of lactic acid bacteria for production of an immunoregulatory composition, wherein the number of the bacteria bound to the uromodulin (Umod) protein is larger than or equivalent to the number of the *Lactobacillus acidophilus* CL-92 strain bound to the uromodulin (Umod) protein.

[14] A kit for screening for lactic acid bacteria having immunoregulatory functions comprising the uromodulin (Umod) protein.

This patent application claims priority from Japanese Patent Application No. 2013-083235 filed on Apr. 11, 2013, and Japanese Patent Application No. 2013-254371 filed on Dec. 9, 2013, and it includes part or all of the content as disclosed in the descriptions thereof.

Effects of the Invention

According to the method of the present invention, lactic acid bacteria having strong immunoregulatory functions can be screened for in vitro in a simple and rapid manner by using the number thereof bound to the Umod protein as an indicator. In comparison with conventional screening methods involving the use of disease animal models or cultured cells, accordingly, the time and labor required for the screening procedure can be reduced significantly.

EMBODIMENTS FOR CARRYING OUT THE INVENTION

Figure 1:
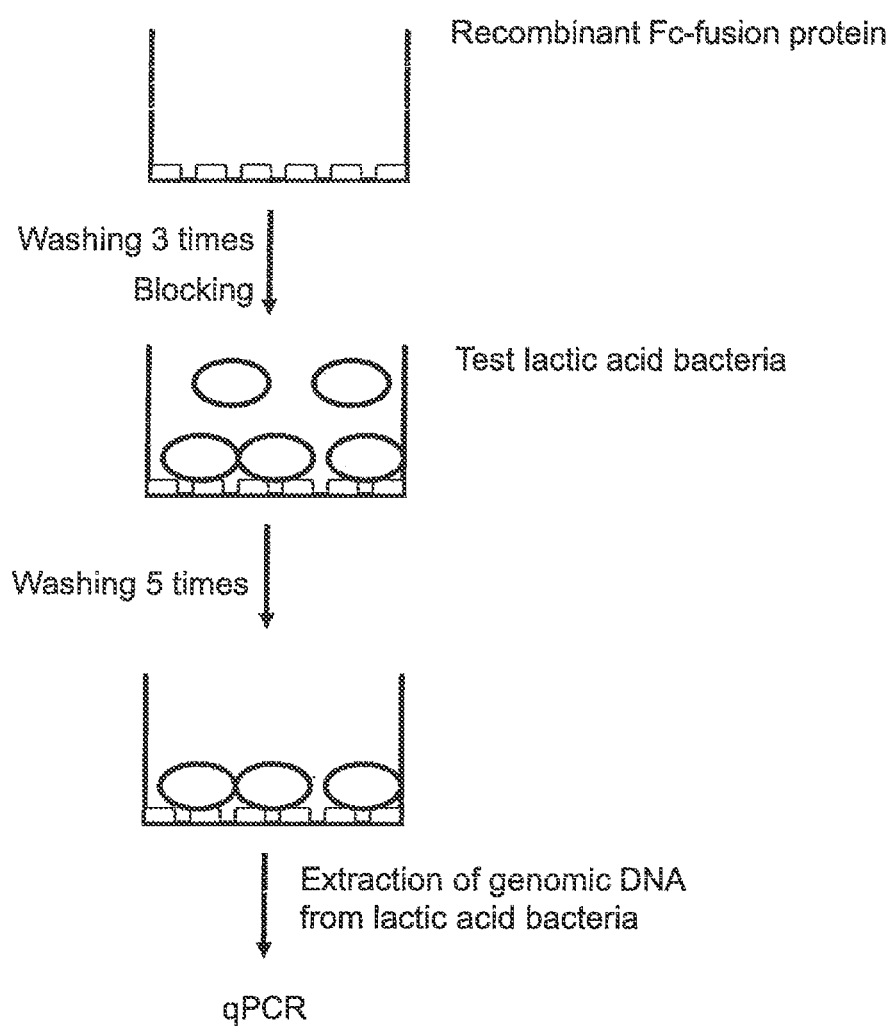
FIG. 1 shows a procedure of the method for screening for lactic acid bacteria according to the present invention.

The method for screening for lactic acid bacteria having immunoregulatory functions according to the present invention involves the use of the binding of test lactic acid bacteria to the uromodulin (Umod) protein as an indicator. Specifically, the method for screening for lactic acid bacteria having immunoregulatory functions according to the present invention comprises determining the number of test lactic acid bacteria bound to the Umod protein and selecting test lactic acid bacteria as the lactic acid bacteria having strong immunoregulatory functions when the number of the test lactic acid bacteria bound to the Umod protein is larger than or equivalent to the number of the *Lactobacillus acidophilus* CL-92 strain as the reference (control) strain bound to the Umod protein.

The uromodulin (Umod) protein used for the screening method according to the present invention is a glycoprotein with a molecular weight of approximately 85 kDa separated and purified from the urine sampled from a pregnant woman by Muchmore and Decker in 1985. As physiological functions thereof, activity of binding to inflammatory cytokines, such as interleukin-1 (IL-1) and a tumor necrosis factor (TNF), and activity of inhibiting T cells and monocytes are known. Umod is also referred to as the Tamm-Horsfall protein (THP).

The Umod protein used in the present invention may be a naturally occurring, synthetic, or recombinant protein. While a human-derived Umod protein is preferable, a Umod protein derived from a non-human mammal such as a mouse or another organism species may be used. The Umod protein is known, and relevant nucleotide sequence information is available from the GenBank. For example, the nucleotide sequence encoding the human-derived Umod protein (Protein ID AAA36799.1) is registered under GenBank Accession No. M17778, the nucleotide sequence encoding the mouse-derived Umod protein (Protein ID NP_033496.1) is registered under GenBank Accession No. NM_009470.4, and the nucleotide sequence encoding the rat-derived Umod protein (Protein ID AAA42319.1) is registered under GenBank Accession No. M63510.

The Umod protein can be prepared in accordance with a known technique. For example, a recombinant Umod protein is preferably prepared via genetic engineering. A recombinant protein may be prepared in a cell system or a cell-free system.

While a Umod protein may be used without any processing, a Umod protein labeled with an arbitrary marker substance may be used. Examples of marker substances include a fluorescent substance, a radioisotope (e.g., $^{125}$I, $^{3}$H, $^{14}$C, and $^{35}$S), a chemiluminescent substance, biotin, a marker protein, and a peptide tag. Examples of marker proteins include an antibody Fc region, alkaline phosphatase, and horse radish peroxidase (HRP). Examples of peptide tags include FLAG, 6×His or 10×His comprising 6 or 10 histidine (His) residues, and influenza hemagglutinin (HA) fragments.

Test lactic acid bacteria may be of any strains belonging to, for example, the genus *Lactobacillus, Lactococcus, Bifidobacterium, Leuconostoc, Streptococcus, Enterococcus, Pediococcus, Weissella,* or *Oenococcus*. Examples of lactic acid bacteria belonging to the genus *Lactobacillus* include *Lactobacillus acidophilus, Lactobacillus brevis, Lactobacillus casei, Lactobacillus delbrueckii, Lactobacillus fermentum, Lactobacillus helveticus, Lactobacillus kefir, Lactobacillus paracasei, Lactobacillus plantarum, Lactobacillus bulgaricus, Lactobacillus rhamnosus, Lactobacillus salivarius, Lactobacillus johnsonii, Lactobacillus gasseri, Lactobacillus amylovorus, Lactobacillus crispatus,* and *Lactobacillus gallinarum*. Examples of lactic acid bacteria belonging to the genus *Lactococcus* include *Lactococcus lactis, Lactococcus plantarum,* and *Lactococcus rafinolactis*. Examples of lactic acid bacteria belonging to the genus *Bifidobacterium* include *Bifidobacterium infantis, Bifidobacterium breve, Bifidobacterium longum, Bifidobacterium pseudolongum, Bifidobacterium bifidum, Bifidobacterium animalis, Bifidobacterium adolescentis, Bifidobacterium catenulatum,* and *Bifidobacterium pseudocatenulatum*. Examples of lactic acid bacteria belonging to the genus *Leuconostoc* include *Leuconostoc lactis* and *Leuconostoc mesenteroides*. Examples of lactic acid bacteria belonging to the genus *Streptococcus* include *Streptococcus thermophiles* and *Streptococcus lactis*. Examples of lactic acid bacteria belonging to the genus *Enterococcus* include *Enterococcus faecalis, Enterococcus durans,* and *Enterococcus faecium*. An example of lactic acid bacteria belonging to the genus *Pediococcus* is *Pediococcus pentosaceus*. Examples of lactic acid bacteria belonging to the genus *Weissella* include *Weissella cibaria, Weissella confusa,* and *Weissella halotolerans*. An example of lactic acid bacteria belonging to the genus *Oenococcus* is *Oenococcus oeni*.

The present invention relates to a method for screening for lactic acid bacteria having immunoregulatory functions, lactic acid bacteria obtained by such method, and an immunoregulatory composition containing such lactic acid bacteria. The immune system functions to eliminate substances that are recognized as foreign matter by an organism. The immune system is essential to life and it is correlated with many vital activities. A majority of cells associated with the immune system exist in the intestinal tract, and the immunoregulatory composition according to the present invention regulates the immune system throughout the body via the cells existing in the intestinal tract. The term "immunoregulatory functions" used herein refers to actions of acting on the natural immune system and the acquired immune system so as to control abnormally excessive or deficient activity of the immune system in the cases of diseases caused thereby. Specific examples of such functions include restoration of reduced immune responses, suppression of overactive immune responses, and regulation of the immune balance.

More specific examples include effects of suppressing allergies, such as pollinosis, perennial allergic rhinitis, atopic dermatitis, and asthma, effects of suppressing inflammatory diseases, effects of suppressing auto immune diseases, effects of suppressing cancers, and effects of protection against infections. The "restoration of reduced immune responses" is understood as encompassing immunostimulating effects, such as anti-virus and anti-bacterial effects, realized by potentiating Th1 and activating NK cells, dendritic cells, and macrophages. The "suppression of overactive immune response" encompasses suppression of Th1, Th2, and Th17 and induction of regulatory T cells. The "regulation of the immune balance" encompasses activity of modulating T cells (normalization of the Th1, Th2, Th17, and regulatory T cell ratio), activity of regulating antibody production (suppression of IgE antibody production and enhancement of IgA antibody production), and activity of regulating inflammatory and anti-inflammatory cytokines (induction of regulatory T cells by TGF-β and regulation of differentiation induction of Th17). In addition, the term "immunoregulatory functions" refers to any activities, including activity of suppressing IgE production, activity of regulating the Th1/Th2 balance toward Th1 dominance, and anti-allergic effects based on accelerated TGF-β production.

Specifically, the method for screening for lactic acid bacteria having immunoregulatory functions according to the present invention comprises the following steps:

(a) bringing test lactic acid bacteria into contact with a uromodulin (Umod) protein;

(b) determining the number of the test lactic acid bacteria bound to the uromodulin (Umod) protein;

(c) comparing the number of bonds determined in (b) with the number of the *Lactobacillus acidophilus* CL-92 strain bound to the uromodulin (Umod) protein (control number of bonds); and (d) selecting lactic acid bacteria exhibiting the number of bonds larger than or equivalent to the control number of bonds as lactic acid bacteria having immunoregulatory functions from among the test lactic acid bacteria based on the results of (c).

In Step (a), test lactic acid bacteria are first brought into contact with the Umod protein. The conditions under which test lactic acid bacteria are brought into contact with the Umod protein are not particularly limited, provided that test lactic acid bacteria bind to the Umod protein. For example, test lactic acid bacteria are applied to a support on which the Umod protein is immobilized, and the reaction is allowed to proceed for a given period of time.

The Umod protein may be immobilized on a support, such as an ELISA plate, a microarray, or a chromatography column. An ELISA plate or a microarray is preferable in order to extensively process many test lactic acid bacteria in a single operation. The Umod protein can be immobilized on a support in accordance with a conventional technique. For example, the Umod protein may be applied to an ELISA plate, the resultant may be allowed to stand overnight so as to immobilize the Umod protein on the ELISA plate, wells may be washed with PBS, and BSA/PBS may be added thereto, so as to block the wells at room temperature.

In Step (b), the number of test lactic acid bacteria bound to the Umod protein is determined. According to a preferable embodiment, the number of test lactic acid bacteria bound to the Umod protein can be determined on the basis of the gene amount of the lactic acid bacteria bound to the Umod protein. Such gene amount can be determined via, for example, hybridization involving the use of an oligo(poly) nucleotide hybridizing to the marker gene of the lactic acid bacteria as a probe, or via gene amplification involving the use of an oligonucleotide hybridizing to the marker gene of the lactic acid bacteria as primers. Specific examples include the DNA probe method, PCR, and in situ hybridization. Quantitative PCR targeting the marker gene of the lactic acid bacteria is particularly preferable. As a marker gene of lactic acid bacteria, the 16S rRNA gene exhibiting high degrees of homology among lactic acid bacteria can be used. Probes and primers used for the method described above can be adequately designed on the basis of the sequence information of the 16S rRNA gene, and they can be adequately prepared using an appropriate oligonucleotide synthesizer.

Alternatively, the number of test lactic acid bacteria bound to the Umod protein can be determined via, for example, culture, the calculation of total cell numbers (nucleic acid stain), the activity staining method (CFDA, CTC), the DVC method, the qDVC method, the microcolony method, the fluorescent antibody method, FISH, DVC-FISH, or SEM-ISH.

In Step (c), subsequently, the number of test lactic acid bacteria bound to the Umod protein determined in Step (b) is compared with the number of the *Lactobacillus acidophilus* CL-92 strain bound to the Umod protein (the control number of bonds) determined in the same manner as described above. The *Lactobacillus acidophilus* L-92® strain, which corresponds to the *Lactobacillus acidophilus* CL-92 strain, is deposited under Accession Number FERM BP-4981 at the Patent Organism Depositary, the National Institute of Technology and Evaluation, has satisfactory effects of improving the "Th1/Th2 balance" associated with allergies. The *Lactobacillus acidophilus* CL-92 strain has the effect of ameliorating pollinosis and the effect of ameliorating perennial allergic rhinitis caused by mites and house dust, and this has been confirmed by the tests involving human subjects. In the screening method according to the present invention, the CL-92 strain can be used as a reference strain having desirable immunoregulatory functions, and a strain exhibiting ability of binding to the Umod protein equivalent thereto can also be used as a reference strain. When the screening method according to the present invention is employed in order to select a lactic acid bacterial strain having stronger immunoregulatory functions, it is preferable that a strain exhibiting ability of binding to the Umod protein higher than or equivalent to that of the CL-92 strain be used as a reference strain. Examples of reference strains other than the CL-92 strain include the *Lactobacillus fermentum* CP1753 strain, the *Lactobacillus fermentum* CP1299 strain, the *Lactobacillus johnsonii* CP1544 strain, the *Lactobacillus helveticus* CP2151 strain, the *Lactobacillus delbrueckii* subsp. *bulgaricus* CP2189 strain, the *Lactobacillus delbrueckii* subsp. *bulgaricus* CP973 strain, the *Lactobacillus acidophilus* CP1613 strain, and the *Lactobacillus brevis* CP287 strain, which are described later as lactic acid bacterial strains wherein the number of the lactic acid bacteria bound to the Umod protein is larger than or equivalent to the number of the *Lactobacillus acidophilus* CL-92 strain bound to the Umod protein, and strains having an ability of binding to the Umod protein larger than or equivalent to that of the strains described above.

Test lactic acid bacteria may be live bacteria or dead bacteria. Dead bacteria that have been crushed may be used. Bacterial strains can be crushed with the use of methods and equipment known in the art by means of, for example, physical crushing or enzymatic lysis. Physical crushing may be carried out via wet processing in the form of a bacteria suspension or dry processing in the form of a bacteria powder. For example, physical crushing may be carried out via agitation involving the use of a homogenizer, a ball mill, a bead mill, the DYNO-mill, or a satellite mill, it may be carried out with the application of pressure using a jet mill, a French press, or a cell crusher, or it may be carried out via filtration through a filter. By means of enzymatic lysis, a bacteria cell wall can be broken using an enzyme, such as lysozyme.

In Step (d), at the end, lactic acid bacteria exhibiting the number of bonds larger than or equivalent to the control number of bonds are selected as candidate lactic acid bacteria having immunoregulatory functions from among test lactic acid bacteria on the basis of the results attained in Step (c). A case in which the number of test lactic acid bacteria bound to the Umod protein can be determined to be obviously large without conducting a comparison with the control number of bonds is within the scope of "a large number of bonds."

In the screening method of the present invention, a reagent used for determining the number of test lactic acid bacteria bound to the Umod protein may be combined in advance to prepare a kit. A kit may include at least the Umod protein. In addition, a kit can include an immobilization support, a reference strain; i.e., the *Lactobacillus acidophilus* CL-92 strain, primers and probes used for detecting lactic acid bacteria, a fluorescent reagent, instruction sheets describing the method of using the kit, and other components.

By the screening method of the present invention, lactic acid bacteria with strong immunoregulatory functions; specifically, the *Lactobacillus fermentum* CP1299 strain, the *Lactobacillus acidophilus* CP1613 strain, and the *Lactobacillus fermentum* CP1753 strain, were selected. The present invention provides such lactic acid bacteria having immunoregulatory functions.

The *Lactobacillus fermentum* CP1299 strain, the *Lactobacillus acidophilus* CP1613 strain, and the *Lactobacillus fermentum* CP1753 strain were on deposit as of Jan. 18, 2013 with the Patent Microorganisms Depositary (NPMD), the National Institute of Technology and Evaluation (#122, 2-5-8 Kazusakamatari, Kisarazu-shi, Chiba, 292-0818, Japan).

*Lactobacillus fermentum* CP1299 strain: Accession Number NITE BP-1512 (Identification: CP1299)

*Lactobacillus acidophilus* CP1613 strain: Accession Number NITE BP-1513 (Identification: CP1613)

*Lactobacillus fermentum* CP1753 strain: Accession Number NITE BP-1514 (Identification: CP1753)

DNAs extracted from the *Lactobacillus fermentnum* CP1299 strain, the *Lactobacillus acidophilus* CP1613 strain, and the *Lactobacillus fermentum* CP1753 strain were amplified by PCR using primers for amplifying 16S rDNAs in lactic acid bacteria, and the nucleotide sequences of 16S rDNAs were determined. As a result, these DNAs were found to comprise the nucleotide sequences as shown in SEQ ID NOs: 1, 2, and 3. Also, strains analogous to the CP1299 strain, the CP1613 strain, and the CP1753 strain that have 16S rDNAs highly homologous to 16S rDNAs of such strains can be used as strains having immunoregulatory functions. The term "high homology" used herein refers to 98% or higher, preferably 99% or higher, more preferably 99.5% or higher, and most preferably 100% homology to the nucleotide sequences (SEQ ID NOs: 1, 2, and 3) of 16S rDNAs of the CP1299 strain, the CP1613 strain, and the CP1753 strain. As long as a strain has immunoregulatory functions greater than or equivalent to immunoregulatory functions of the CP1299 strain, the CP1613 strain, and the CP1753 strain, such strains may be mutants thereof. A mutant can be either a natural mutant or a mutant resulting from a conventional means for artificial mutation with the aid of, for example, ultraviolet rays, radiation, N-methyl-N'-nitro-N-nitrosoguanidine, or a nucleotide base analog, such as nitrosoguanidine or bromouracil.

By performing the steps similar to those for the screening method described above, the immunoregulatory functions of the test lactic acid bacteria can be evaluated, and lactic acid bacteria having immunoregulatory functions can be produced.

The lactic acid bacteria obtained by the screening method can be adequately mixed with other ingredients without damaging the immunoregulatory functions thereof and the resultant can be provided in the form of an immunoregulatory composition, such as a pharmaceutical product or a food or beverage product. Lactic acid bacteria that are active ingredients of the immunoregulatory composition according to the present invention have been employed in connection with the dietary habits of humans for a very long time. Accordingly, lactic acid bacteria are safe and can be used for those ranging from young children to elderly people for long periods of time. A single type or a plurality of types of lactic acid bacteria may be incorporated as an active ingredient.

The immunoregulatory composition according to the present invention comprises, as an active ingredient, lactic acid bacteria having strong immunoregulatory functions obtained by the screening method described above. Accordingly, such composition can be administered on a daily basis for the purpose of prevention or amelioration of diseases caused by or associated with reduced immune responses or an immune imbalance (e.g., a Th2-dominant state). Examples of such diseases include, but are not limited to, allergic diseases (e.g., pollinosis, atopic dermatitis, bronchial asthma, allergic rhinitis, allergic conjunctivitis, allergic enterogastritis, food allergy, hives, hemolytic anemia, thrombocytopenic purpura, myasthenia gravis, Goodpasture's syndrome, acute glomerulonephritis, rheumatic arthritis, collagen disease, serum disease, viral hepatitis, allergic alveolitis, contact dermatitis, and angioedema), inflammatory bowel diseases (e.g., ulcerative colitis and Crohn's disease), autoallergic disease (e.g., multiple sclerosis, systemic erythematodes, chronic rheumatoid arthritis, type I diabetes mellitus, and pernicious anemia), cancers (e.g., colorectal cancer, lung cancer, gastric cancer, breast cancer, colorectal cancer, and bladder cancer), and infections (e.g., infections caused by HIV, influenza virus, norovirus, and rotavirus, and enterohemorrhagic *E. coli* infection).

When the immunoregulatory composition according to the present invention is used for a pharmaceutical product, pharmaceutically acceptable base materials, carriers, and additives that are adequately selected in accordance with dosage forms may be used to prepare various forms of pharmaceutical preparations that can be orally or parenterally administered throughout the body or topically in accordance with various conventional techniques. Examples of additives include excipients, diluents, binders, lubricants, disintegrators or disintegration adjuvants, solubilizers, stabilizers, preservatives, antiseptics, fillers, dispersants, lubricants, humectants, buffers, and aroma chemicals.

The pharmaceutical product according to the present invention can be administered orally or parenterally, and it is preferably administered orally. When the pharmaceutical product according to the present invention is to be administered orally, it may be prepared in the form of, for example, tablets (including sugar-coated tablets), capsules, granules, powders, pills, liquid medicines for internal use, suspensions, emulsions, or syrups. Alternatively, it may be in the form of a dry product to be redissolved at the time of administration. When the pharmaceutical product according to the present invention is to be administered parenterally, it may be prepared in the form of, for example, injections (e.g., hypodermic injections, intravenous injections, intramuscular injections, or intraperitoneal injections), drops, or suppositories. An injection is provided in the form of a unit-dose ampule or multiple-dose container.

When the pharmaceutical product according to the present invention is used for a medicine intended for prevention and/or treatment of allergic diseases and inflammatory bowel diseases, it can be administered to a mammalian, such as a human, mouse, rat, rabbit, dog, or cat. A dose of the pharmaceutical product according to the present invention can be adequately determined in accordance with the disease type, the age, the sexuality, the body weight, and the severity of symptoms of the subject. For example, a dose of the pharmaceutical product according to the present invention per day is preferably $1\times10^7$ to $1\times10^{11}$ cells, and more preferably $1\times10^9$ to $1\times10^{11}$ cells, in terms of the cell count of the lactic acid bacteria as an active ingredient.

The term "food or beverage product" used in the present invention refers to any health food, functional food, nutritional supplementary food, or Food for Specified Health Uses. A food or beverage product may be in a form suitable for edible use, such as a solid, liquid, granulated, particulate, powdery, capsule (hard or soft), cream, or paste form. Examples of dosage forms particularly suitable for health foods and functional foods include tablets, capsules, granules, and powders. For example, a health food in a tablet form can be produced by compressing a formulation containing the lactic acid bacteria having immunoregulatory functions obtained via the method of the present invention into a given form, preparing a kneaded product of the lactic acid bacteria moistened with water or a solvent such as an alcohol in a given form, or pouring the lactic acid bacteria into a given mold.

Examples of food or beverage products include, but are not particularly limited to, beverage products, such as soft drinks, carbonated drinks, nutritional drinks, fruit drinks, and milk drinks, including liquid concentrates and conditioning powders of such beverage products, dairy products, such as processed milk, fermented milk, yogurt, butter, and cheese, breads, noodles, confectioneries, processed marine and livestock products, processed soy products, such as tofu, and oil and fat and processed products thereof. Beverage products that can be easily and continuously ingested are preferable.

When the immunoregulatory composition according to the present invention is used for a food or beverage product, an effective amount of lactic acid bacteria as an active ingredient may be incorporated into starting materials for producing such a food or beverage product. Alternatively, lactic acid bacteria may be incorporated into a product after the process of production.

The food or beverage product according to the present invention may adequately comprise common additives in accordance with product type, in addition to food materials. Any additives that are acceptable from the viewpoint of food hygiene can be used, and examples thereof include sweeteners, such as sugar, fructose, isomerized liquid sugar, glucose, aspartame, and stevia, acidulants, such as citric acid, malic acid, and tartaric acid, excipients, such as dextrin and starch, fillers, binders, diluents, aroma chemicals, food colors, buffers, thickeners, gelatinizers, stabilizers, preservatives, emulsifiers, dispersants, suspending agents, and antiseptic agents.

The amount of lactic acid bacteria to be incorporated into the food or beverage product according to the present invention is not particularly limited, provided that the immunoregulatory functions can be satisfactorily exerted. Such amount may adequately be determined by taking, for example, the amount of the target food or beverage product to be generally ingested, the form of the food or beverage product, efficacy and effects, a taste, preference, and cost into consideration. For example, the amount of the food or beverage product according to the present invention to be ingested per day is preferably $1\times10^7$ to $1\times10^{11}$ cells, and more preferably $1\times10^9$ to $1\times10^{11}$ cells, in terms of the cell count of the lactic acid bacteria as an active ingredient. In the case of a beverage product, for example, the amount of lactic acid bacteria to be incorporated may be determined in accordance with the amount of the beverage that is generally ingested per day, and the amount of lactic acid bacteria to be incorporated per beverage may be determined on the basis of the amount of the lactic acid bacteria to be ingested per day.

EXAMPLES

The present invention is described in greater detail with reference to the following examples, although the technical scope of the present invention is not limited to these examples.

[Example 1] Evaluation of Number of Lactic Acid Bacteria Bound to Umod (1) Preparation of Test Lactic Acid Bacteria About 20 lactic acid bacterial strains belonging to the genus *Lactobacillus* were used for the experiment. The *Lactobacillus acidophilus* CL-92 strain was used as a reference strain having immunoregulatory functions. The *Lactobacillus acidophilus* CL-92 strain was deposited under Deposit Accession No. FERM BP-4981 on Mar. 3, 1994, at the National Institute of Bioscience and Human-Technology Agency of Industrial Science and Technology, located at 1-3, Higashi 1-chome, Tsukuba-shi, Ibaraki-ken 305, JAPAN. These strains were subjected to static culture in MRS medium (Difco) at 37° C. for 20 hours, washed three times with PBS, and then suspended in PBS.

(2) Preparation of Fc-mUmod Fusion Protein

A mouse-derived Umod protein (positions 1 to 616 of SEQ ID NO: 5) was ligated to the Fc domain of human IgG1 to prepare a fusion protein (Fc-mUmod) in accordance with the description of Hase K. et al., Uptake through glycoprotein 2 of FimH1 bacteria by M cells initiates mucosal immune response, Nature 2009, 462: 226-31. The mUmod (mouse Umod) sequence (SEQ ID NO: 4) was amplified using the forward primer: 5'-CGCAGATCTAC-CATGGGGATCCCTTTGACC-3' (SEQ ID NO: 6) and the reverse primer: 5'-CGCGTCGACCTTGGACACTGAG-GCCTGG-3' (SEQ ID NO: 7) and it was then cloned into the pcDNA3 vector (Invitrogen) into which the Fc domain had been inserted using the BglII and SalI restriction enzymes.

The vector into which Fc-mUmod had been cloned was introduced into the HEK293T cell derived from a human fetal nephrocyte and cultured for 7 to 10 days. The Fc-mUmod protein secreted into the supernatant was collected and then purified using the HiTrap protein AHP affinity column (GE Healthcare).

(3) In Vitro Binding Assay

The Fc-mUmod protein and hIgG as the control Fc protein were diluted to 5 µg/ml in PBS, 50 µl of the dilution was applied to a 96-well plate, and proteins were immobilized at 4° C. overnight. Each well was washed three times with 200 μl of PBS, 200 μl of a 1% BSA/PBS solution was applied thereto, and the wells were then blocked at room temperature for 2 hours. After the block solution was removed, a suspension of test lactic acid bacteria in PBS ($10^6$ cells/50 μl) was applied to wells in amounts of 50 μl each, followed by incubation at room temperature for 2 hours. After the wells had been washed five times with 200 μl of PBS, PBS was completely removed.

With the use of NucleoSpin™ Tissue (Takara), DNA was extracted from the bacterial strains bound to the plate in accordance with the protocol. The extracted DNA was subjected to real-time PCR as a template with the use of universal primers (i.e., F: 5'-AACTGGAG-GAAGGTGGGGAT-3' (SEQ ID NO: 8); and R: 5'-AG-GAGGTGATCCAACCGCA-3' (SEQ ID NO: 9)), so as to quantify the number of strains bound to Fc-mUmod and hIgG in accordance with the protocol included in the SYBR™ Premix Ex Taq™ II (Tli RNaseH Plus) (Takara). The procedures for the in vitro binding assays described above are shown in FIG. 1.

The number of strains bound to hIgG was subtracted from the number of strains bound to Fc-mUmod, and the resulting number was designated as the number of Umod bonds. Table 1 shows the results of calculation of the numbers of Umod bonds for the 14 types of test lactic acid bacterial strains, including the reference strain.

TABLE 1

| Lactic acid bacterial strains | Number of Umod bonds ($\log_{10}$) |
|---|---|
| Lactobacillus fermentum CP1753 | 5.4 |
| Lactobacillus fermentum CP1299 | 5.3 |
| Lactobacillus johnsonii CP1544 | 4.7 |
| Lactobacillus helveticus CP2151 | 4.3 |
| Lactobacillus delbrueckii subsp. bulgaricus CP2189 | 4.3 |
| Lactobacillus delbrueckii subsp. bulgaricus CP973 | 4.2 |
| Lactobacillus acidophilus L-92 | 4.1 |
| Lactobacillus acidophilus CP1613 | 4.0 |
| Lactobacillus brevis CP287 | 3.9 |
| Lactobacillus acidophilus CP734 | 3.7 |
| Lactobacillus acidophilus CP23 | 3.5 |
| Lactobacillus casei CP2517 | 3.5 |
| Lactobacillus gasseri CP793 | 3.1 |
| Lactobacillus rhamnosus CP1270 | 2.7 |

As shown in Table 1, lactic acid bacterial strains exhibiting the number of Umod bonds larger than, equivalent thereto, and smaller than the number of Umod bonds exhibited by the Lactobacillus acidophilus CL-92 strain (the reference strain) (i.e., the control number of bonds) were observed.

[Lactic Acid Bacterial Strains Exhibiting the Number of Umod Bonds Larger than or Equivalent to the Control Number of Bonds]

Lactobacillus fermentum CP1753, Lactobacillus fermentum CP1299, Lactobacillus johnsonii CP1544, Lactobacillus helveticus CP2151, Lactobacillus delbrueckii subsp. bulgaricus CP2189, Lactobacillus delbrueckii subsp. bulgaricus CP973, Lactobacillus acidophilus CP1613, and Lactobacillus brevis CP287

[Lactic Acid Bacterial Strains Exhibiting the Number of Umod Bonds Smaller than the Control Number of Bonds]

Lactobacillus acidophilus CP734, Lactobacillus acidophilus CP23, Lactobacillus casei CP2517, Lactobacillus gasseri CP793, and Lactobacillus rhamnosus CP1270

[Example 2] Evaluation of Anti-Allergic Effect (OVA-IgE Reduction) of Lactic Acid Bacteria (1) Preparation of Test Lactic Acid Bacteria The lactic acid bacterial strains belonging to the genus Lactobacillus that had been subjected to inspection to determine the number of Umod bonds in Example 1 were used for the experiment. The Lactobacillus acidophilus CL-92 strain was used as a reference strain having anti-allergic effects. These strains were subjected to static culture in MRS medium (Difco) at 37° C. for 20 hours and then washed three times with physiological saline (a 0.85% (w/v) NaCl solution). The bacterial strains were suspended in physiological saline, sterilized at 85° C., lyophilized, and then pulverized.

(2) Measurement of the Degree of OVA-IgE Reduction

Groups of mice each consisting of five 6-week-old female Balb/c mice (Charles River Laboratories Japan, Inc.) were subjected to the experiment. On the day the experiment was initiated and for three days thereafter, ovalbumin (OVA) was intraperitoneally administered together with an aluminum hydroxide gel adjuvant twice, so as to prepare allergic mouse models. The mice were forced to orally ingest a solution of the test lactic acid bacteria in tap water (about $10^9$ cells/ml) in an amount of 0.1 ml per 10 g of body weight every day from 3 days after the experiment. Tap water was administered to the control mice. Blood samples were obtained from the abdominal portions of the inferior vena cava 14 days later, the mice were allowed to bleed to death, and the mesenteric lymph nodes were isolated and then subjected to cold storage overnight using the RNAlater (Applied Biosystems).

The sampled blood was allowed to stand at room temperature for at least one hour so as to lead blood clots to aggregate, and a serum sample was obtained via centrifugation at 1,000 rpm for 10 minutes. The OVA-specific IgE antibody titers in the blood sera of the mice were assayed via ELISA using the Revis OVA-IgE mouse assay reagent (Shibayagi Co. Ltd.). The OVA-specific IgE antibody titer of the mice to which the Lactobacillus acidophilus CL-92 strain had been administered was designated 100%, and reductions in the OVA-specific IgE antibody titers of the mice to which various types of lactic acid bacteria had been administered were determined. The results are shown in Table 2.

TABLE 2

| Lactic acid bacterial strains | Degree of OVA-IgE reduction |
|---|---|
| Lactobacillus fermentum CP1753 | 17% |
| Lactobacillus fermentum CP1299 | 55% |
| Lactobacillus johnsonii CP1544 | 32% |
| Lactobacillus helveticus CP2151 | 20% |
| Lactobacillus delbrueckii subsp. bulgaricus CP2189 | 19% |
| Lactobacillus delbrueckii subsp. bulgaricus CP973 | −11% |
| Lactobacillus acidophilus L-92 | 0% |
| Lactobacillus acidophilus CP1613 | 15% |
| Lactobacillus brevis CP287 | 30% |
| Lactobacillus acidophilus CP734 | −13% |
| Lactobacillus acidophilus CP23 | −14% |
| Lactobacillus casei CP2517 | 43% |
| Lactobacillus gasseri CP793 | −2% |
| Lactobacillus rhamnosus CP1270 | −38% |

As shown in Table 2, the degree of OVA-IgE reduction were high in the mice to which the lactic acid bacterial strains that were confirmed to exhibit the number of Umod bonds larger than or equivalent to the control number of bonds in Example 1, that is, the *Lactobacillus fermentum* CP1753 strain, the *Lactobacillus fermentum* CP1299 strain, the *Lactobacillus johnsonii* CP1544 strain, the *Lactobacillus helveticus* CP2151 strain, the *Lactobacillus delbrueckii* subsp. *bulgaricus* CP2189 strain, the *Lactobacillus acidophilus* CP1613 strain, and the *Lactobacillus brevis* CP287, had been administered. In contrast, no reduction was observed in the OVA-IgE level in the mice to which the lactic acid bacterial strains that were confirmed to exhibit the number of Umod bonds less than the control number of bonds in Example 1, that is, the *Lactobacillus rhamnosus* CP1270 strain, the *Lactobacillus acidophilus* CP23 strain, and the *Lactobacillus acidophilus* CP734 strain, had been administered.

Figure 2:
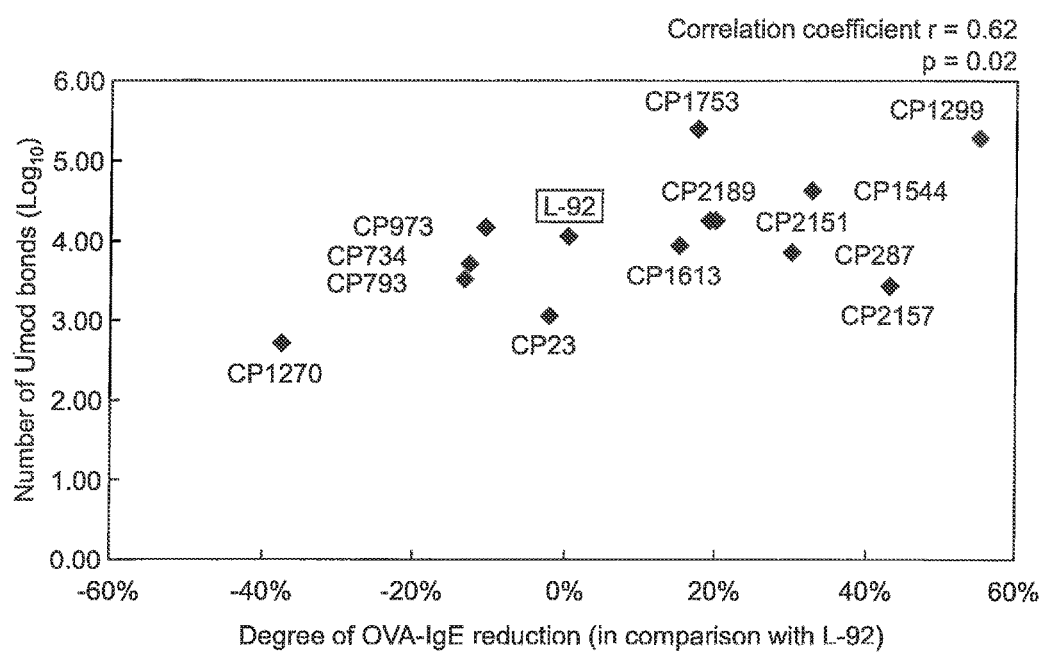
FIG. 2 is a plot showing the correlation between the number of test lactic acid bacteria bound to Umod and the degree of OVA-IgE reduction. L-92 indicates CL-92 (FERM BP-4981).

(3) Correlation Between the Number of Umod Bonds and the Degree of OVA-IgE Reduction FIG. 2 shows plots of the number of Umod bonds determined in Example 1 along the vertical axis and the degree of OVA-IgE reduction determined in (2) above along the horizontal axis. The results of plotting demonstrate that the number of Umod bonds is correlated with OVA-IgE and that lactic acid bacterial strains exhibiting the number of Umod bonds larger than or equivalent to that of the *Lactobacillus* CL-92 strain (i.e., CP1753, CP1299, CP1613, CP1544, CP287, CP2151, and CP2189) show a significant reduction in OVA-IgE level and have strong anti-allergic effects.

[Example 3] Evaluation of Anti-Allergic Effect (Productions of Cytokines IL-4, IL-10, and IL-12) of Lactic Acid Bacterial Strains (1) Preparation of Test Lactic Acid Bacteria Test lactic acid bacterial strains were prepared in the same manner as in Example 2 (1).

(2) Measurement of Cytokine Expression Level in Mesenteric Lymph Nodes

The expression levels of cytokines (IL-4, IL-10, and IL-12) in the mesenteric lymph nodes isolated from the allergic mouse models prepared in Example 2 (2) were determined. At the outset, the mesenteric lymph nodes isolated from the mice were introduced into an RLT solution included in an RNeasy Mini Kit (Qiagen) supplemented with 2-mercaptoethanol, sliced using scissors, and then homogenized using a homogenizer (Polytron). Thereafter, total RNAs were extracted in accordance with the instructions included in the RNeasy Mini Kit, and the concentration and the purity of the total RNA were determined using the Agilent 2100 Bioanalyser (Agilent Technologies).

With the use of 1 μg of total RNA as a template, cDNA was obtained using a transcriptor first strand cDNA synthesis kit (Roche). PCR was carried out using a Lightcycler 480 SYBR Green I Master (Roche), and the amplification products were detected and quantified using a Light Cycler PCR and a real-time detection system (Roche). The nucleotide sequences of the primers used for amplifying the cytokine genes are given below.

```
(Primers for IL-4 amplification)
                                          (SEQ ID NO: 10)
IL-4_F: 5'-CCCCAGCTAGTTGTCATCCTG-3'

(SEQ ID NO: 11)
IL-4_R: 5'-CGCATCCGTGGATATGGCTC-3'

(Primers for IL-10 amplification)
                                          (SEQ ID NO: 12)
IL-10_F: 5'-ACAGCCGGGAAGACAATAACT-3'

(SEQ ID NO: 13)
IL-10_R: 5'-GCAGCTCTAGGAGCATGTGG-3'

(Primers for IL-12 amplification)
                                          (SEQ ID NO: 14)
IL-12_F: 5'-CAATCACGCTACCTCCTCTTTT-3'

(SEQ ID NO: 15)
IL-12_R: 5'-CAGCAGTGCAGGAATAATGTTTC-3'

(Primers for GAPDH amplification)
                                          (SEQ ID NO: 16)
GAPDH_F: 5'-AGGTCGGTGTGAACGGATTTG-3'

(SEQ ID NO: 17)
GAPDH_R: 5'-GGGGTCGTTGATGGCAACA-3'
```

The expression levels of the genes were corrected using the GAPDH expression level and the relative expression levels were determined on the basis of the expression levels in the control mice. The results are shown in Table 3 below.

TABLE 3

| Lactic acid bacterial strains | |
|---|---|
| | IL-4 |
| *Lactobacillus fermentum* CP1753 | 0.44 |
| *Lactobacillus fermentum* CP1299 | 0.82 |
| *Lactobacillus acidophilus* L-92 | 1.22 |
| *Lactobacillus acidophilus* CP1613 | 3.05 |
| *Lactobacillus acidophilus* CP23 | 5.18 |
| | IL-10 |
| *Lactobacillus fermentum* CP1753 | 0.42 |
| *Lactobacillus fermentum* CP1299 | 0.43 |
| *Lactobacillus acidophilus* L-92 | 0.64 |
| *Lactobacillus acidophilus* CP1613 | 0.54 |
| *Lactobacillus acidophilus* CP23 | 0.81 |
| | IL-12/IL4 |
| *Lactobacillus fermentum* CP1753 | 3.67 |
| *Lactobacillus fermentum* CP1299 | 1.85 |
| *Lactobacillus acidophilus* L-92 | 0.71 |
| *Lactobacillus acidophilus* CP1613 | 1.01 |
| *Lactobacillus acidophilus* CP23 | 0.82 |

As shown in Table 3, the *Lactobacillus fermentum* CP1753 strain and the *Lactobacillus fermentum* CP1299 strain exhibiting large numbers of Umod bonds exhibited low IL-4 and IL-10 expression levels and high IL-12/IL-4 levels (i.e., Th1 dominance over Th2). In contrast, the *Lactobacillus acidophilus* CP23 strain exhibiting a small number of Umod bonds exhibited high IL-10 expression levels and low IL-12/IL-4 levels (i.e., Th2 dominance over Th1).

(3) Correlation Between the Number of Umod Bonds and Cytokine Expression Level

Figure 3:
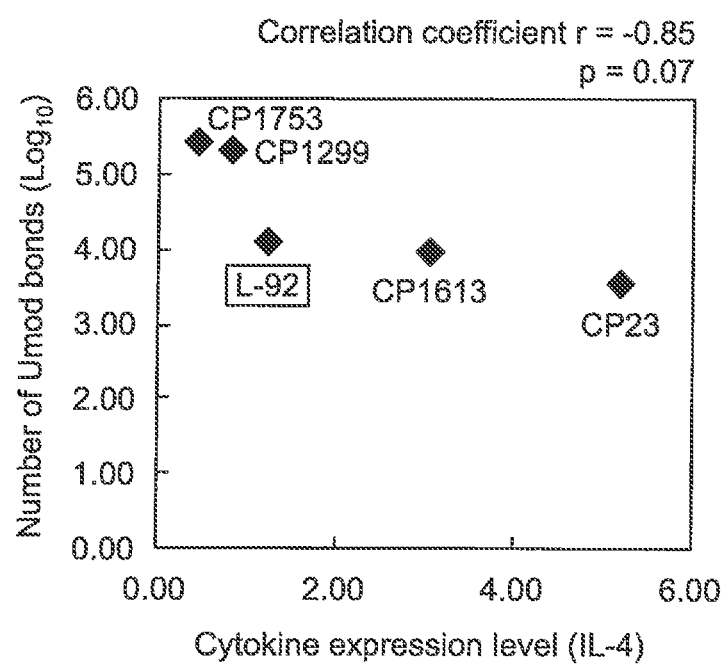
FIG. 3 is a plot showing the correlation between the number of test lactic acid bacteria bound to Umod and the cytokine (IL-4) expression level. L-92 indicates CL-92 (FERM BP-4981).
Figure 4:
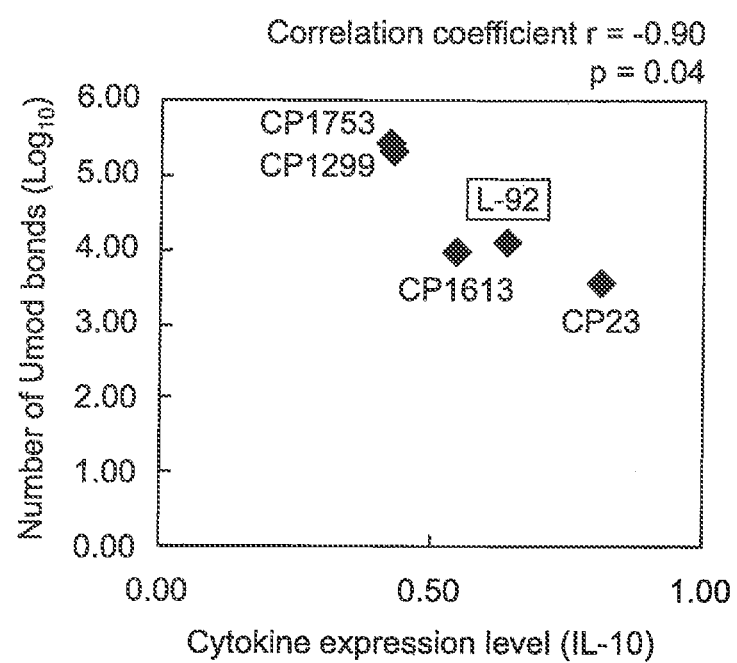
FIG. 4 is a plot showing the correlation between the number of test lactic acid bacteria bound to Umod and the cytokine (IL-10) expression level. L-92 indicates CL-92 (FERM BP-4981).
Figure 5:
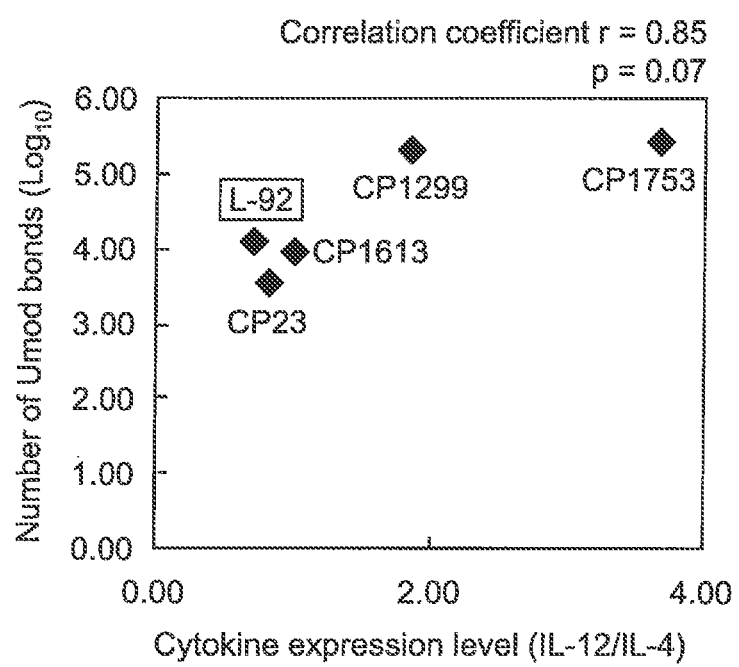
FIG. 5 is a plot showing the correlation between the number of test lactic acid bacteria bound to Umod and the cytokine (IL-12/IL-4) expression level. L-92 indicates CL-92 (FERM BP-4981).

FIGS. 3 to 5 each show plots of the number of Umod bonds determined in Example 1 along the vertical axis and the expression levels of cytokines (IL-4, IL-10, and IL-12/IL-4, respectively) determined in (2) above along the horizontal axis. The results of plotting demonstrate that the number of Umod bonds is correlated with the cytokine expression level and that lactic acid bacterial strains exhibiting the number of Umod bonds larger than or equivalent to that of the *Lactobacillus* CL-92 strain (i.e., CP1753, CP1299, and CP1613) exhibit low Th2 cytokine (IL-4 and IL-10) expression levels (FIGS. 3 and 4) and high Th1 cytokine (IL-12) expression levels (FIG. 5). Accordingly, the lactic acid bacterial strains exhibiting the number of Umod bonds that is larger than or equivalent to that of the *Lactobacillus acidophilus* CL-92 strain regulate the Th1/Th2 balance toward Th1 dominance. This indicates that such strains exert strong anti-allergic effects.

[Example 4] Evaluation of Anti-Allergic Effect (Production of Cytokine, TGF-β) of Lactic Acid Bacterial Strains (1) Measurement of Cytokine (TGF-β) Expression Level in Mesenteric Lymph Nodes The expression levels of cytokine (TGF-β) in the mesenteric lymph nodes isolated from the allergic mouse models prepared in Example 2 (2) were determined. The TGF-β expression level was determined by preparing RNA in the same manner as in Example 3 (2) and conducting amplification by PCR. The nucleotide sequences of the primers used for amplifying the TGF-β gene are given below.

```
(Primers for TGF-β amplification)
                                         (SEQ ID NO: 18)
TGF-β_F: 5'-AGCTGGTGAAACGGAAGCG-3'

(SEQ ID NO: 19)
TGF-β_R: 5'-GCGAGCCTTAGTTTGACAGG-3'
```

The TGF-β expression level was corrected using the GAPDH expression level and the relative expression level was determined on the basis of the expression level in the control mice. The results are shown in Table 4 below.

TABLE 4

| Lactic acid bacterial strains | TGF-β |
| --- | --- |
| *Lactobacillus fermentum* CP1753 | 1.09 |
| *Lactobacillus fermentum* CP1299 | 1.82 |
| *Lactobacillus johnsonii* CP1544 | 1.03 |

TABLE 4-continued

| Lactic acid bacterial strains | TGF-β |
| --- | --- |
| *Lactobacillus helveticus* CP2151 | 0.45 |
| *Lactobacillus delbrueckii* subsp. *bulgaricus* CP2189 | 0.94 |
| *Lactobacillus delbrueckii* subsp. *bulgaricus* CP973 | 0.42 |
| *Lactobacillus acidophilus* L-92 | 1.01 |
| *Lactobacillus acidophilus* CP1613 | 1.14 |
| *Lactobacillus brevis* CP287 | 0.65 |
| *Lactobacillus acidophilus* CP734 | 0.79 |
| *Lactobacillus acidophilus* CP23 | 1.24 |
| *Lactobacillus casei* CP2517 | 0.83 |
| *Lactobacillus gasseri* CP793 | 0.22 |
| *Lactobacillus rhamnosus* CP1270 | 0.66 |

(2) Correlation Between the Number of Umod Bonds and TGF-β Expression Level

Figure 6:
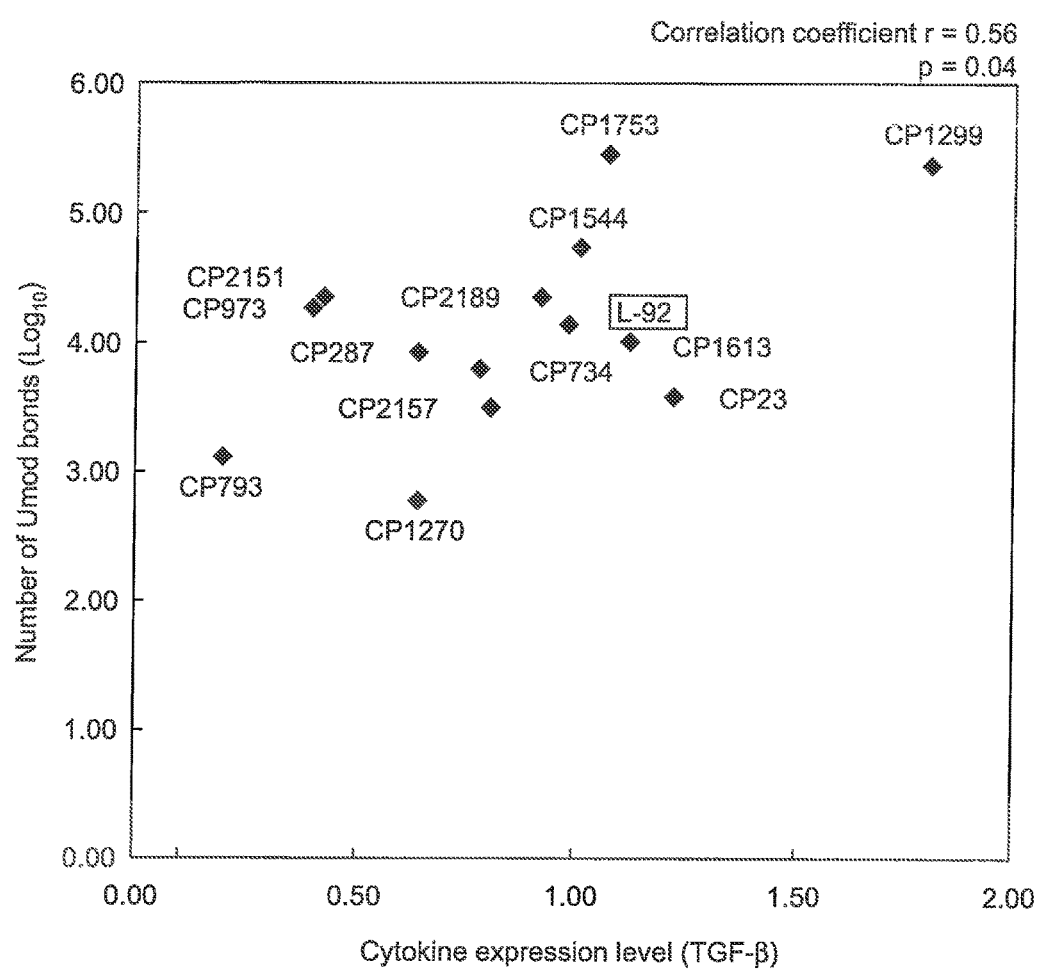
FIG. 6 is a plot showing the correlation between the number of test lactic acid bacteria bound to Umod and the cytokine (TGF-β) expression level. L-92 indicates CL-92 (FERM BP-4981).

FIG. 6 shows plots of the number of Umod bonds determined in Example 1 along the vertical axis and the TGF-β expression level determined in (1) above along the horizontal axis. The results of plotting demonstrate that the number of Umod bonds is correlated with the TGF-β expression level. In particular, lactic acid bacterial strains exhibiting large numbers of Umod bonds (i.e., CP1753, CP1299, and CP1613) exhibited high TGF-β expression levels (FIG. 6). This demonstrates that lactic acid bacterial strains exhibiting large numbers of Umod bonds accelerate the production of TGF-β, which is a factor associated with suppression of allergic inflammation. Thus, such lactic acid bacterial strains exert strong anti-allergic effects.

The test results described above demonstrate that lactic acid bacteria exerting immunoregulatory effects can be screened for using the number of lactic acid bacteria bound to Umod as an indicator.

INDUSTRIAL APPLICABILITY

The present invention is applicable in the field of production of probiotic food and beverage products.

All publications, patents, and patent applications cited herein are incorporated herein by reference in their entirety.

The invention claimed is:

1. A method for obtaining a lactic acid bacteria strain having immunoregulatory activity comparable to immunoregulatory activity exhibited by a *Lactobacillus acidophilus* CL-92 strain (FERM BP-4981), the method comprising the steps of
   (1) providing a lactic acid bacteria strain of interest having unknown immunomodulatory activity, as a test strain,
wherein the test strain is not a *Lactobacillus acidophilus* CL-92 strain (FERM BP-4981), and
   wherein the test strain is suspended in a suitable culture medium, and also providing a *Lactobacillus acidophilus* CL-92 strain (FERM BP-4981) suspended in a suitable culture medium,
   (2) separately contacting the respective suspended *Lactobacillus acidophilus* CL-92 strain (FERM BP-4981) and the respective suspended test strain with a uromodulin (Umod) protein under identical conditions, and
   (3) when the number of the test lactic acid bacteria bound to the Umod protein is larger than, or equivalent to, the number of the *Lactobacillus acidophilus* CL-92 strain (FERM BP-4981) bacteria bound to the Umod protein to provide a Umod binding test strain, obtaining the Umod binding test bacteria.

2. The method according to claim 1, wherein the number of bound bacteria is determined based on the amount of a lactic acid bacteria marker gene measured in the lactic acid bacteria bound to the uromodulin (Umod) protein.

3. The method of claim 1, further comprising growing the obtained lactic acid bacteria in culture.

4. The method of claim 1, further comprising combining the obtained lactic acid bacteria with one or more of a pharmaceutically acceptable excipient or carrier, to provide a pharmaceutical product.

5. The method of claim 1, further comprising combining the obtained lactic acid bacteria with one or more of an edible food or beverage component, to provide a food or beverage product.

6. The method of claim 2, wherein the lactic acid bacteria marker gene is lactic acid 16S rRNA.

7. The method of claim 1, wherein the Umod protein is a mouse-derived Umod protein (positions 1 to 616 of SEQ ID NO: 5) ligated to the Fc domain of human IgG1 to provide an Fc-mUmod fusion protein.

8. The method of claim 1, wherein each suspended culture comprises the same numbers of bacteria per milliliter, and each being under identical conditions.

9. The method of claim 1, wherein the lactic acid bacteria are alive.

10. The method of claim 1, wherein the Umod protein is immobilized on a support.

\* \* \* \* \*